(12) United States Patent
Klein

(10) Patent No.: US 10,121,036 B1
(45) Date of Patent: Nov. 6, 2018

(54) SYSTEM AND METHOD FOR COLLECTING ENVIRONMENTAL TEST DATA

(71) Applicant: Danny Klein, Culver City, CA (US)

(72) Inventor: Danny Klein, Culver City, CA (US)

(*) Notice: Subject to any disclaimer, the term of this patent is extended or adjusted under 35 U.S.C. 154(b) by 0 days.

(21) Appl. No.: 15/640,367

(22) Filed: Jun. 30, 2017

(51) Int. Cl.
| *G06K 7/10* | (2006.01) |
| *G06K 7/14* | (2006.01) |
| *G01N 21/78* | (2006.01) |
| *G01N 33/02* | (2006.01) |
| *G01N 33/18* | (2006.01) |
| *G01N 33/24* | (2006.01) |
| *G01N 33/00* | (2006.01) |

(52) U.S. Cl.
CPC ......... *G06K 7/10722* (2013.01); *G01N 21/78* (2013.01); *G06K 7/1413* (2013.01); *G01N 33/0062* (2013.01); *G01N 33/02* (2013.01); *G01N 33/18* (2013.01); *G01N 33/24* (2013.01)

(58) Field of Classification Search
CPC .. G06K 7/10722; G06K 7/1413; G01N 21/78; G01N 33/0062; G01N 33/02; G01N 33/18; G01N 33/24
USPC ....... 235/380, 375, 462.41, 462.1; 250/336.1
See application file for complete search history.

(56) References Cited

U.S. PATENT DOCUMENTS

| 5,591,974 A * | 1/1997 | Troyer ................... G01D 1/14 250/336.1 |
| 6,097,995 A | 8/2000 | Tipton et al. |
| 7,077,328 B2 | 7/2006 | Krishnaswamy et al. |
| 8,528,822 B2 | 9/2013 | Henry et al. |
| 8,820,630 B2 | 9/2014 | Qu et al. |
| 9,188,466 B2 | 11/2015 | Matsumura |
| 9,417,205 B2 | 8/2016 | Simmons et al. |
| 9,459,200 B2 | 10/2016 | Dupoteau et al. |
| 2005/0187733 A1 * | 8/2005 | Staab ................... G01N 1/02 702/150 |
| 2008/0237040 A1 | 10/2008 | Wessel |
| 2010/0257027 A1 | 10/2010 | Greenberg et al. |
| 2010/0315644 A1 | 12/2010 | Egan et al. |
| 2011/0275162 A1 | 11/2011 | Xie et al. |
| 2013/0032634 A1 | 2/2013 | McKirdy |
| 2016/0357391 A1 | 12/2016 | Nilo et al. |
| 2018/0005095 A1 * | 1/2018 | Schindler, III ..... G06K 17/0022 |

\* cited by examiner

*Primary Examiner* — Karl D Frech

(74) *Attorney, Agent, or Firm* — Select Patents; Ashkon Cyrus

(57) ABSTRACT

The present invention discloses a method for detecting, storing, analyzing and enabling access to collected biological or environmental test data. The method includes providing one or more test packs comprising one or more testing strips or swabs for testing biological or environmental materials. The method further includes testing a targeted material at a targeted location and scanning, via a scanning device connected to a computer network, the one or more testing mediums to create collected test data based on the revealed information of the testing, wherein the scanning takes place a short time after the testing and at the targeted location, and wherein the collected test data includes the time, date and geographical tracking data based on the GPS location of the scanning device at the time of the scanning.

12 Claims, 13 Drawing Sheets

SYSTEM AND METHOD FOR COLLECTING ENVIRONMENTAL TEST DATA

FIELD OF THE INVENTION

The present invention is in the technical field of data collection and analysis. More particularly, the present invention relates to systems and methods for detecting, storing, analyzing and enabling access to collected biological or environmental test data.

BACKGROUND OF THE INVENTION

Global concerns regarding the health and welfare of our food, water and air systems are at an all-time high and growing rapidly each year. Radioactivity, mercury, arsenic, lead, bisphenol A, benzene and a range of other toxins are finding their way into our food, water, soil, consumer products and air supplies, the systems that support them, and ultimately our bodies. Furthermore, humans are discovering an increased range of dangerous and/or disruptive allergens such as gluten, mold and others contained in our food, water, soil, consumer products and air supplies, the systems that support them, and ultimately our bodies.

Prior art test systems and/or methods for detecting environmental toxins may have utilized test strips that exhibit color changes when brought in contact with a test sample. An existing diagnostic system uses test strips that exhibit color changes when brought in contact with a test sample. The color changes of the test strips may be by a dedicated apparatus, or a general-purpose reader apparatus. The reader apparatus may have the functionality of obtaining the color information of the test strips.

However, in the prior art, the collected data may not have been always kept, or it may not have been kept in a fashion that allows for ready retrieval and/or analysis for future problems, and/or for environmental trends and/or correlations, and/or for immediate communication to other local or regional devices or testers. Furthermore, these existing devices may be prohibitively expensive for certain applications. For example, the reader apparatus might not be widely affordable in developing countries where mobile diagnostics are needed the most. The testing kits also provide little incentive for users to go out and test various environmental materials and provide information to the wider public, because of the difficulty in obtaining and maintaining accurate results.

Thus, there exists a need for a system which allows users to easily detect and upload test data, and provide the ability track and report test results.

SUMMARY OF THE INVENTION

The present invention discloses a method for detecting, storing, analyzing and enabling access to collected biological or environmental test data. The method includes providing one or more test packs comprising one or more testing strips or swabs for testing biological or environmental materials.

Embodiments of the present invention disclose providing test strips and swabs to detect the presence of toxins and allergens in food, air, water, soil, consumer products and our bodies. Users scan and input data into a central database, which populates personal profiles, creating a personal map of each user's air, food, water, soil and consumer products quality findings.

Embodiments of the present invention disclose providing test mediums (such as test strips or swabs) in a pack, wherein the testing mediums are packaged in highly portable personal sized packets suitable for a purse or pocket.

Embodiments of the present invention disclose inputting test data into a mobile device. In one embodiment, a user taps on a mobile device the corresponding readout of the test swabs or strips. In another embodiment, a user takes a photo of a test strip or swab by a mobile device for random or full verification. In yet another embodiment, a user scans a corresponding bar code revealed on strip by their mobile device, which then interprets the corresponding bar code results. In yet another embodiment, a user uploads a photo of the swab or strip by a mobile device, which then utilizes existing color recognition technology to interpret upload the data. In yet another embodiment, a user uploads a photo of the swab or strip by a mobile device, and shape and/or alphanumeric recognition technology recognizes and uploads the data. In all cases, such field data will be time and date stamped, geo-track stamped with latitude and longitude, via the location services function of the mobile device.

Further embodiments of the present invention disclose testing a targeted material at a targeted location and scanning, via a scanning device connected to a computer network, the one or more testing mediums to create collected test data based on the revealed information of the testing, wherein the scanning takes place a short time after the testing and at the targeted location, and wherein the collected test data includes the time, date and geographical tracking data based on the GPS location of the scanning device at the time of the scanning;

Further embodiments of the present invention disclose providing user profiles with searchable and scrubbable data points such as location, age, weight, height, gender, nationality, ethnicity, lifestyle, diet, health concerns.

Further embodiments of the present invention disclose pooling test data from all users into a central database. In one embodiment, this test data is scrubbed and sorted, providing a data map of all results worldwide. In yet another embodiment, the central database data pool will be utilized to set up a new global environmental index; much the way a stock market tracks the real-time valuation of a range of stocks, properties and other economic values. The global user field data will be searchable and scrubbable, allowing for the real-time ranking and valuation of the presence of toxins and allergens in food, air, water, soil, consumer products and our bodies. Index results will be searchable and scrubbable and pooled to provide for a wide range of rankings, such as the ranking of consumer products. For example, various brands of bottled water could be ranked by lead or other toxicity. In another example, restaurants or other food service providers could be ranked by a detection of toxins such as mercury in fish. Other examples include rankings of specific geographic locations (such as lakes ranked by arsenic or other toxicity), the rankings of specific buildings or workplace locations (such as locations ranked by airborne mold or other toxicity), or the rankings of specific users or user groups (such as users ranked by nationality, age, gender and amount of glucose or gluten found in blood stream).

Further embodiments of the present invention disclose proving specific pack-bundles for use by academic institutions of all ages and levels. For example, a School pack could provide for the detection of lead and arsenic at the school's drinking fountains, or a youth-targeted field trip directing students to locate toxins and/or allergens in their surrounding community. University packs could contain more sophisticated field and laboratory tests based on specific scientific, environmental, medical, social and/or anthropological disciplined targets, and be directed towards higher learning institutions worldwide to integrate with their existing research programs to stimulate data collection, collaboration, discovery and inter-institutional communication.

DETAILED DESCRIPTION OF THE INVENTION

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The present invention discloses a method for detecting, storing, analyzing and enabling access to collected biological or environmental test data. The method includes providing one or more test packs comprising one or more testing strips or swabs for testing biological or environmental materials. The method further includes testing a targeted material at a targeted location and scanning, via a scanning device connected to a computer network, the one or more testing mediums to create collected test data based on the revealed information of the testing, wherein the scanning takes place a short time after the testing and at the targeted location, and wherein the collected test data includes the time, date and geographical tracking data based on the GPS location of the scanning device at the time of the scanning.

In one embodiment of the present invention, each pack contains materials for testing water, food, air, soil, consumer products and self. Further embodiments of the present invention disclose a user testing a targeted material tested at a targeted location, wherein the test medium reacts with the targeted material to reveal information. In one embodiment, the medium reacts with the targeted material and reveals one or more barcodes based on the reaction. In another embodiment, the test medium reacts with the targeted material to reveal different colors; or shapes, alphabetical, numeric and/or alpha/numeric codes; based on the reaction. In one embodiment, the test packs comprise a specific bundle of testing mediums directed towards a goal objective.

Figure 1:
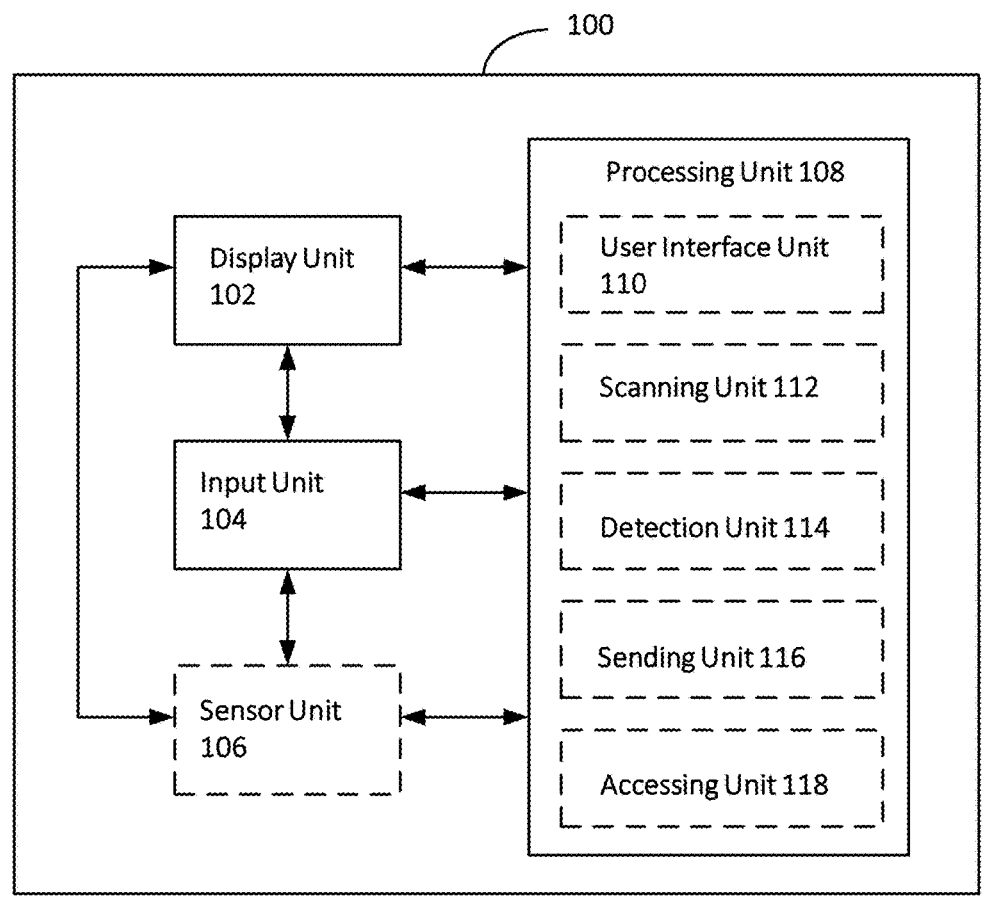
FIG. 1 shows a functional block diagram of an electronic device 101.

In accordance with an embodiment of the invention, FIG. 1 shows a functional block diagram of an electronic device 101.

As shown in FIG. 1, the electronic device 100 includes a display unit 102 configured to display a user interface, an input unit to input test data information, and a processing unit 108 coupled with the display unit 102 and the input unit 104. In some embodiments, the electronic device includes one or more sensor units 106 configured to detect inputs, and the processing unit 108 is also coupled with the one or more sensor units 106. In some embodiments, the one or more sensor units 106 include one or more cameras configured to scan testing materials, and GPS receivers to detect GPS coordinates. The electronic device 100 is preferably a networking electronic device, and provided with communications (e.g., network connection, GSM, satellite connection, Internet) capabilities. The electronic device 100 may be in wireless (and/or wired) communication with at least one remote server. In some embodiments, the processing unit 1308 includes: a user interface unit 110, a scanning unit 112, a detection unit 114, a sending unit 116, and an accessing unit 118.

Figure 9:
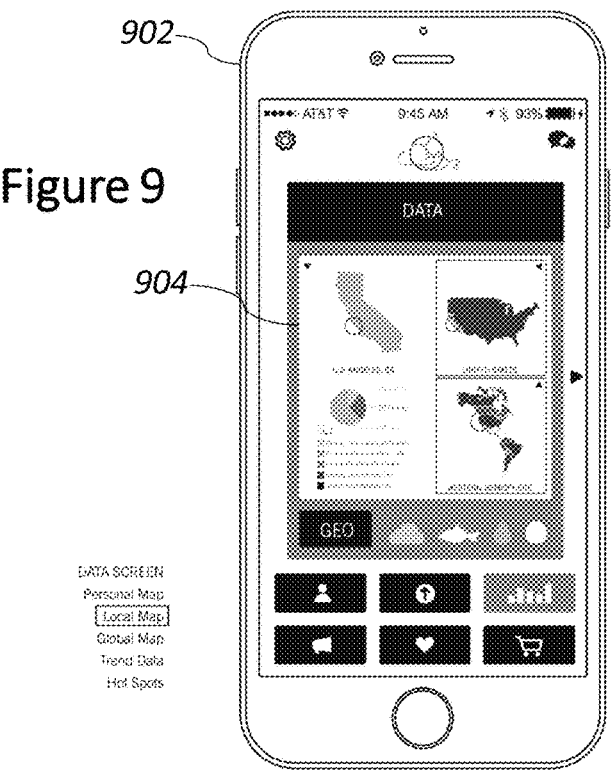
FIG. 9 illustrates an embodiment of the invention where a mobile device displays a local map data screen.
Figure 10:
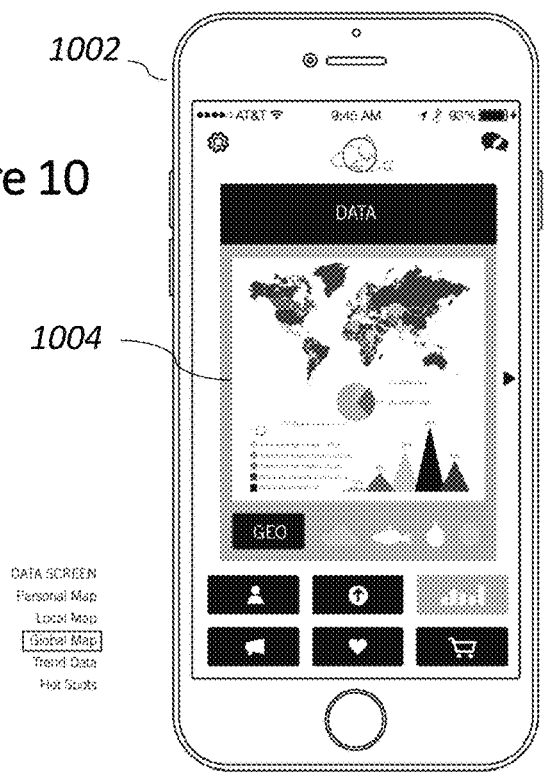
FIG. 10 illustrates an embodiment of the invention where a mobile device displays a global map data screen.
Figure 11:
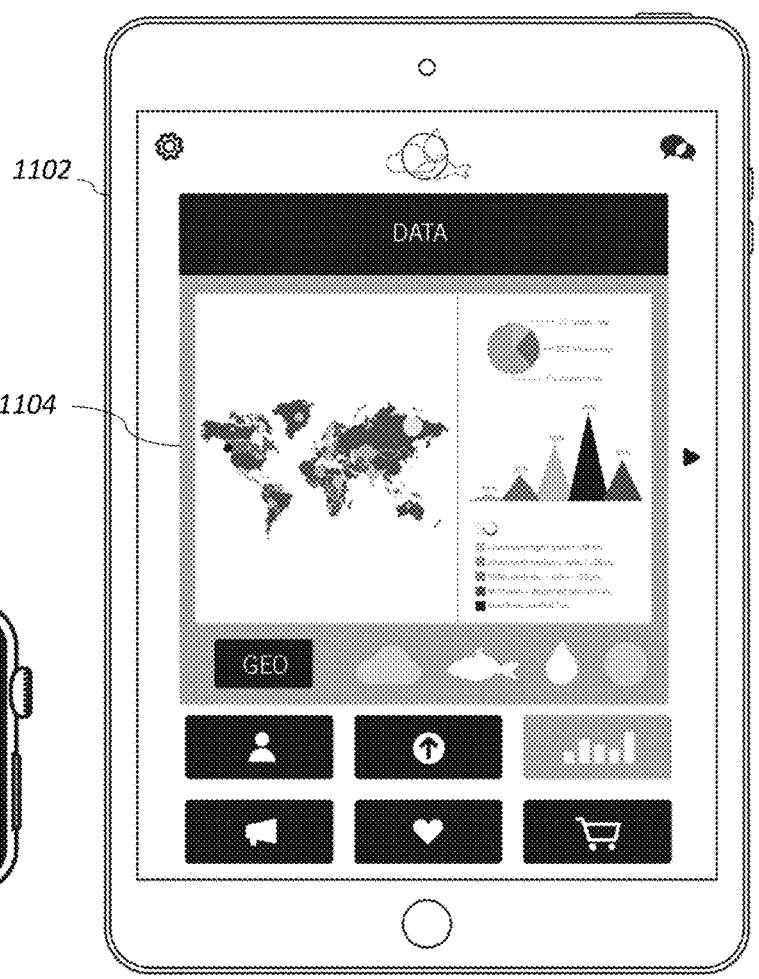
FIG. 11 illustrates an embodiment of the invention where a mobile device displays a global map data screen.
Figure 12:
FIG. 12 illustrates an embodiment of the invention where a mobile device displays a global map data screen.

The electronic device 100 may be a mobile telephone (as shown in FIGS. 3 to 10; 13 to 17), a tablet device (as shown in FIG. 11), or a smartwatch or other wearable tech device (as shown in FIG. 12). According to various other preferred embodiments of the invention, the electronic device 100 may take the form of a virtual reality device or an augmented-reality device. According to some preferred embodiments of the invention, it may be suitable to utilize any electronic device 100 which provides a CPU, camera, GPS unit, and capacity to run, analyze, record and/or transmit the test results.

The processing unit 108 is configured to enable display of a user interface at a first display rate (e.g., with User Interface Unit 110). The processing unit 108 is also configured to, while displaying the user interface: scan (e.g., scanning unit 112) one or more testing material. In one embodiment, the testing material for use with the electronic device, is adapted to receive and operatively react a sample with one or more reagents. The scanning unit operatively detects information from the sample after reaction with the reagents.

The processing unit 108 is further configured to detect (e.g., with detecting unit 114) test data based on the information detected by the scanning unit. In one embodiment, the scanning takes place at a targeted location, and wherein the test data further includes the time, date and geographical tracking data based on the GPS location of the electronic device at the time of the scanning.

The processing unit 108 is further configured to send (e.g., with sending unit 116) the test data to a remote database located on a remote server. In one embodiment, processing unit 108 automatically transmits the test data after detecting the test data. In another embodiment, the user manually sends the test data by pressing a button through the graphical user interface.

The processing unit 108 is further configured to access (e.g., with access unit 118) the test data located on the remote database on the remote server.

The functional blocks of the device are, optionally, implemented by hardware, software, firmware, or a combination thereof to carry out the principles of the various described embodiments. It is understood by persons of skill in the art that the functional blocks described in FIG. 1 are, optionally, combined or separated into sub-blocks to implement the principles of the various described embodiments. Therefore, the description herein optionally supports any possible combination or separation or further definition of the functional blocks described herein.

Figure 2:
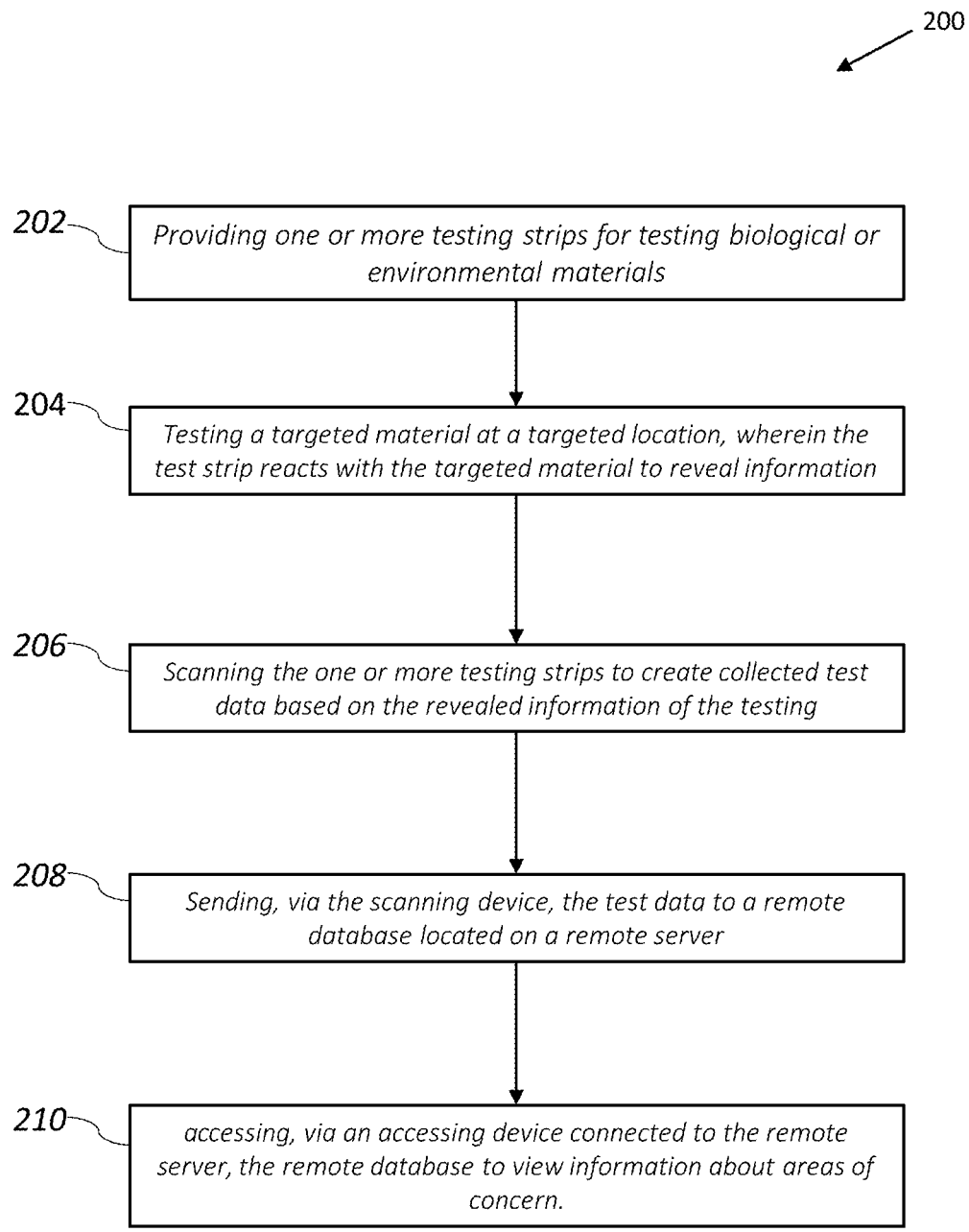
FIG. 2 depicts a flowchart of an example of a process for detecting, storing, analyzing and enabling access to collected biological or environmental test data through a mobile device.

FIG. 2 depicts a flowchart of an example of a process for detecting, storing, analyzing and enabling access to collected biological or environmental test data through a mobile device. In the example of FIG. 2, the flowchart 200 starts at block 202 where one or more test strips are provided for testing biological or environmental materials. Embodiments of the present invention disclose providing test mediums (such as test strips or swabs) in a pack, wherein the testing mediums are packaged in highly portable personal sized packets suitable for a purse or pocket. In one embodiment of the present invention, each pack contains materials for testing water, food, air, soil, consumer products and self.

The flowchart 200 continues to block 204 where a targeted material is tested at a targeted location, wherein the test strip reacts with the targeted material to reveal information. In one embodiment, the test strip reacts with the targeted material and reveals one or more barcodes based on the reaction. In another embodiment, the strip reacts with the targeted material to reveal different colors based on the reaction. In yet another embodiment, the strip reacts with the targeted material to reveal different shapes and/or alphabetical, numerical and/or alphanumeric characters based on the reaction.

The flowchart 200 continues to block 206 where a test strip is scanned by the mobile device to create collected test data based on the revealed information of the testing. In one embodiment, the mobile device scans a barcode revealed on the test strip, and based on the barcode revealed creates collected test data. For example, the collected test information could state:

LEAD: 338.13 cc
0.11.17. 12:34 pm/
GPS: +40.698050 −74.044636.

It can be appreciated that in one embodiment of the present invention, traces of a tested toxin or other harmful material will reveal a barcode on the strip indicating presence of the toxin, allergen or harmful substance while a negative result will show no result. In another embodiment, a negative result will show an alternative barcode. The barcode can reveal information about the type of toxin or harmful material that was detected, based on the detection technology contained within the strip.

Figure 3:
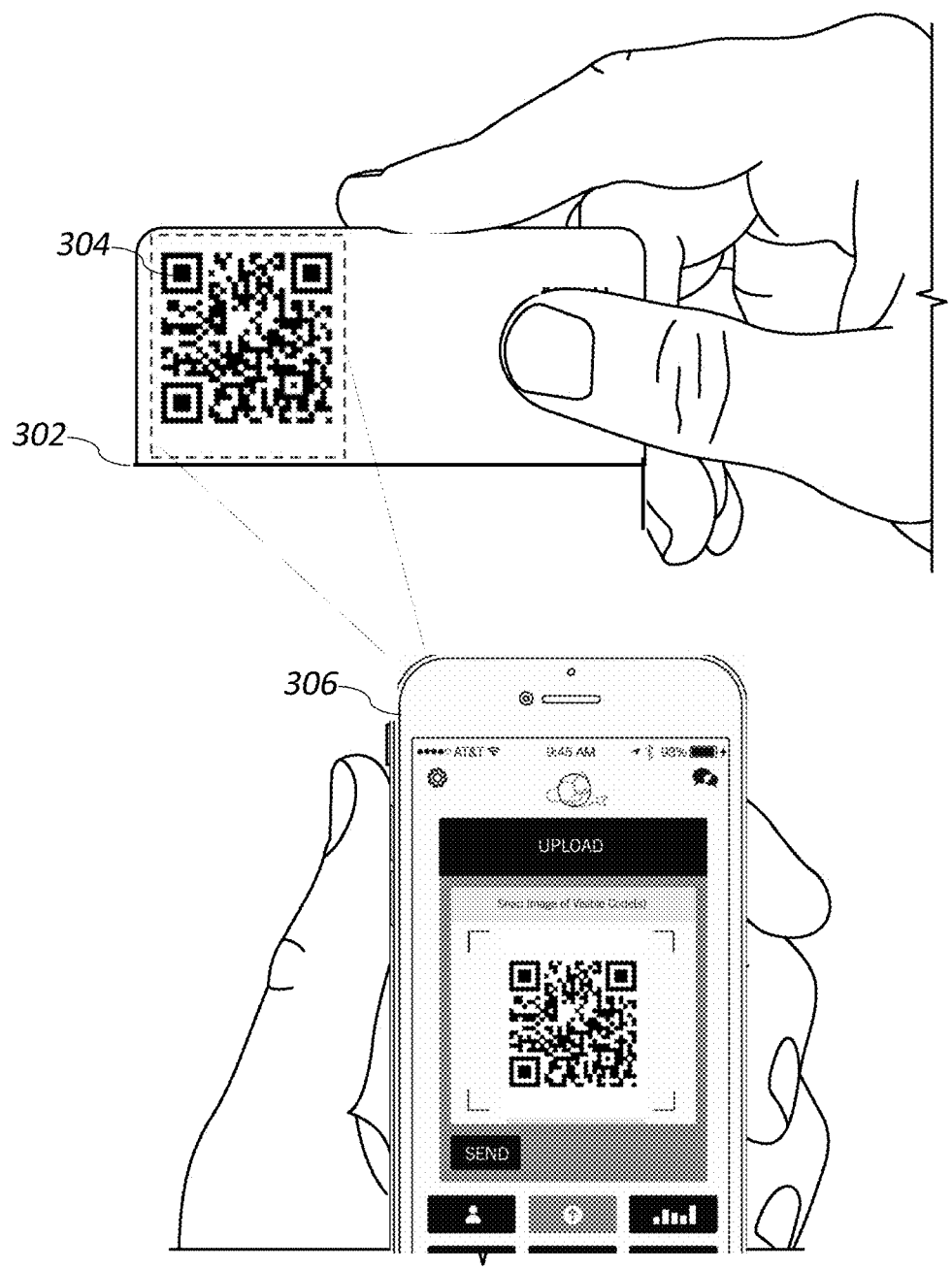
FIG. 3 illustrates an embodiment of the invention where a test strip is scanned by a mobile device to create collected test data based on the revealed information of the testing.

FIG. 3 illustrates an embodiment of the invention where a test strip 302 is scanned by a mobile device 306 to create collected test data based on the revealed information of the testing. A user points a mobile device 306 at the test strip 302 and the barcode 304 is recognized through the camera of the mobile device. In one embodiment, the scanning takes place a short time after the testing and at a targeted location, and wherein the collected test data includes the time, date and geographical tracking data based on the GPS location of the mobile device at the time of the scanning.

Figure 4:
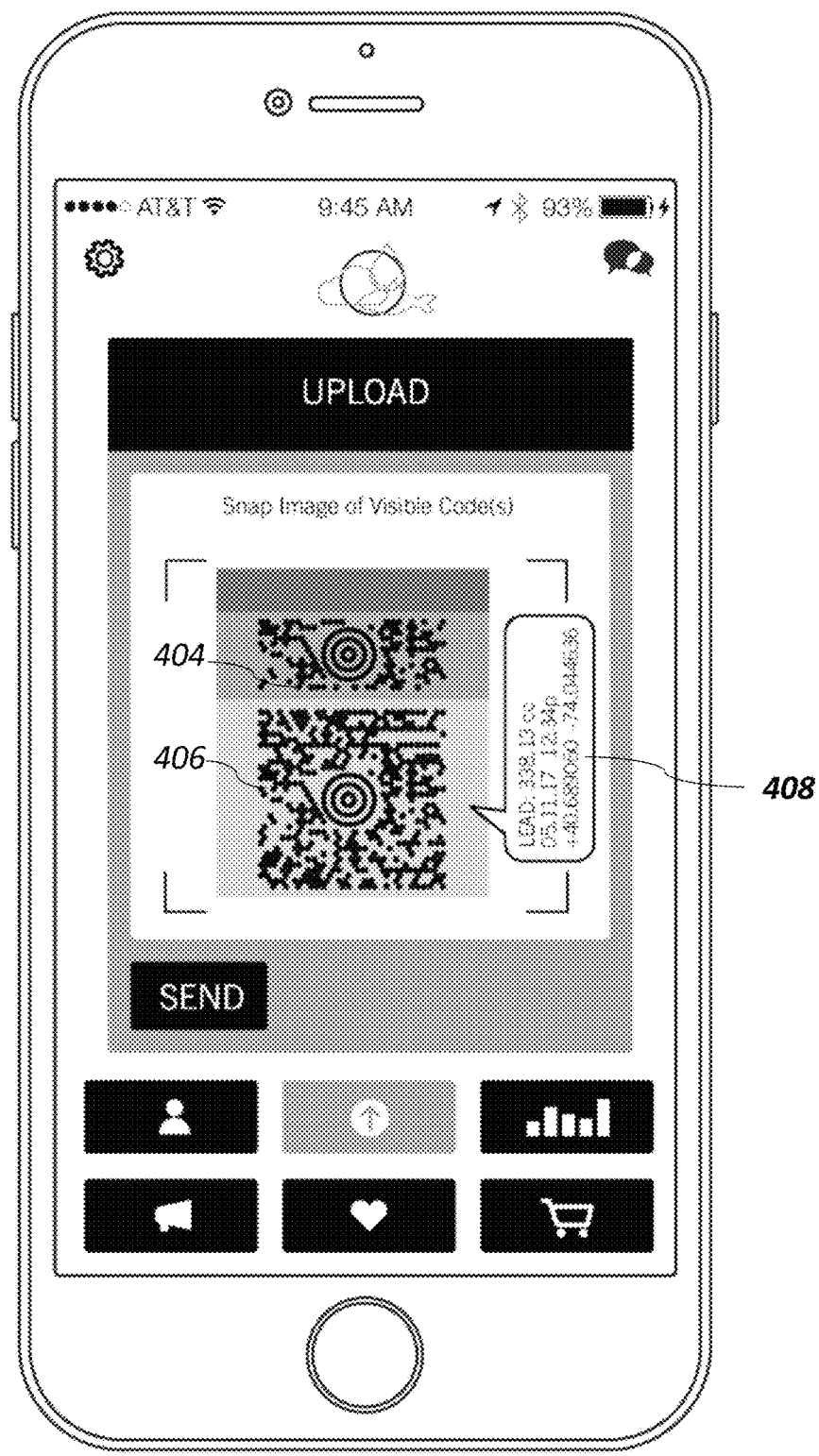
FIG. 4. illustrates an embodiment of the invention where a mobile device has scanned a test strip with revealed information including two barcodes.

FIG. 4. illustrates an embodiment of the invention where a mobile device 402 has scanned a test strip with revealed information including barcodes 404 and 406. That is, in this embodiment, the testing strip can reveal multiple barcodes based on the detection of a toxin or other harmful substance on the testing strip. The mobile phone 402 then scans the multiple barcodes 404 and 406 on the testing strip to create collected test information 408. In one embodiment, the collected test information 408 is displayed immediately after scanning the corresponding barcode.

In one embodiment, each strip is configured to test for the presence of multiple toxins, and each barcode relates to a particular toxin. For example, one strip might be able to test for the presence of lead, arsenic or mercury. The presence of any or all of those would be revealed by its corresponding barcode on the strip.

Figure 5:
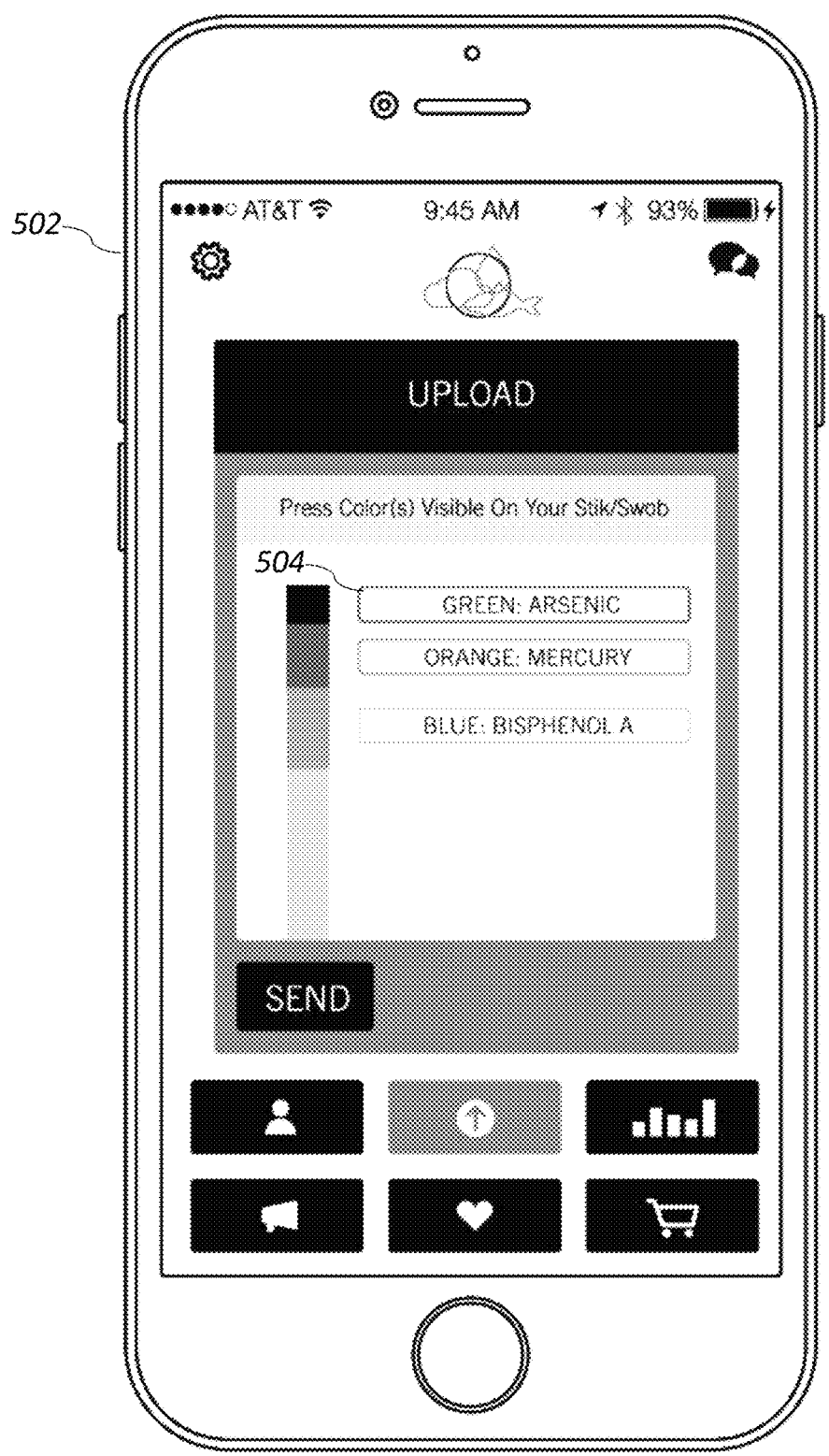
FIG. 5. illustrates an embodiment of the invention where revealed information is manually input into the mobile device by a user.
Figure 6:
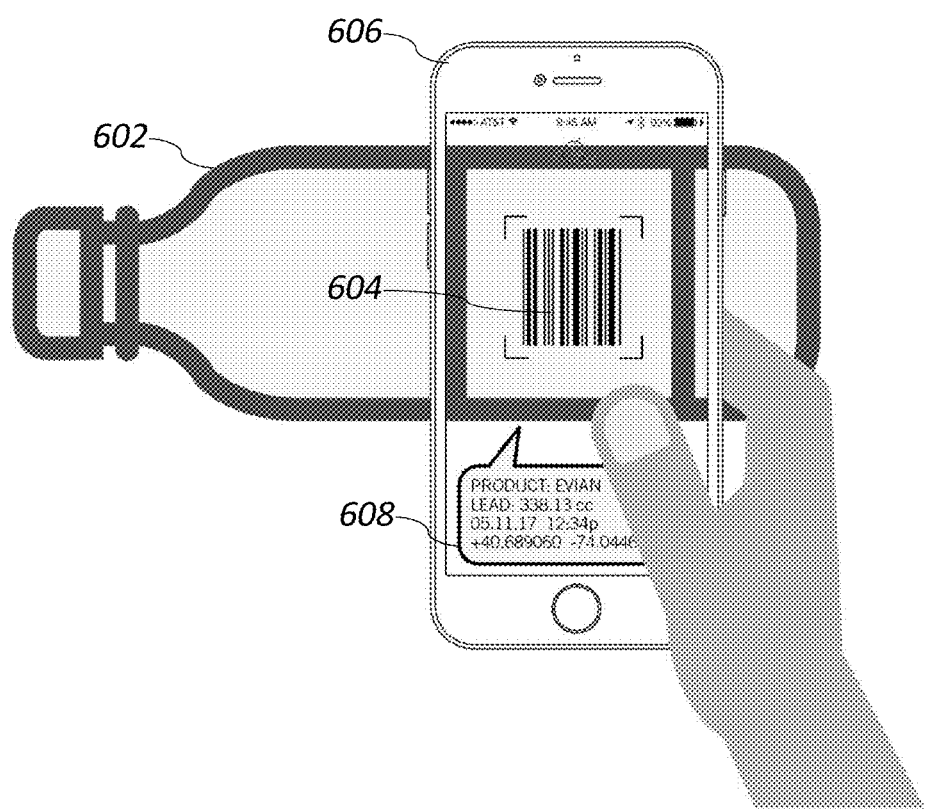
FIG. 6 illustrates an embodiment of the invention where the barcode of a consumer product is scanned.

Further embodiments of the present disclosure are aimed at novel ways of uploading the data detected by the one or more strips into a centralized repository. FIG. 5. illustrates an embodiment of the invention where revealed information is manually input into the mobile device 502 by a user. In one embodiment, the test strip reveals different colors based on the testing. In this embodiment, a user taps on the corresponding readouts area 504 of mobile device 502 based on the corresponding readouts from the test strip. FIG. 6 illustrates an embodiment of the invention where the barcode 604 of a consumer product 602 is scanned by a mobile device 606. In one embodiment, the barcode 604 is scanned shortly after testing the contents of the consumer product 602 with a test strip. Consumer product information 608 is added to the collected test data to be sent to the database. It can be appreciated that this feature of the invention allows a user to quickly and easily upload potential harmful properties of a consumer product to a remote database, such that it will be accessible to all users of the platform.

Figure 7:
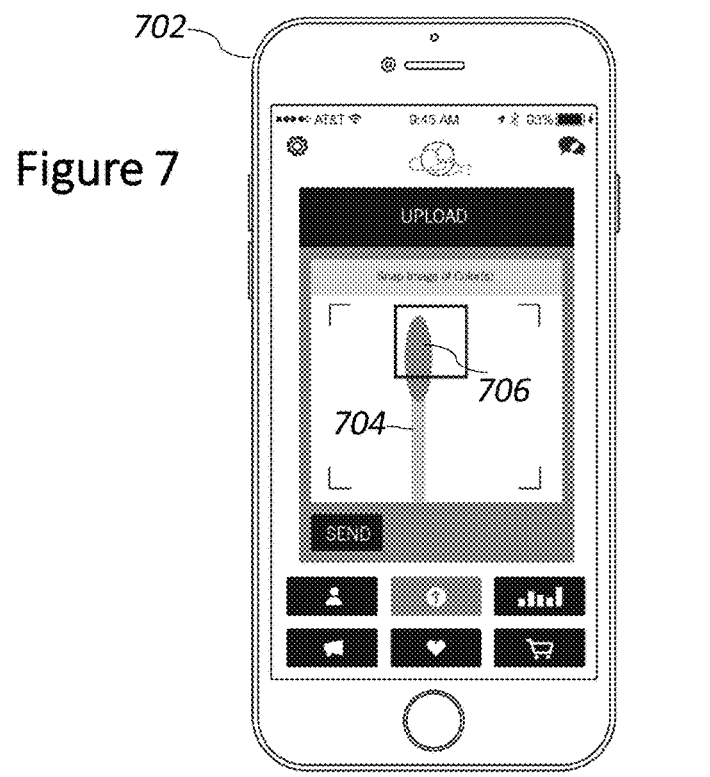
FIG. 7 illustrates an embodiment of the invention where a test swab is scanned by the camera of a mobile device.

FIG. 7 illustrates an embodiment of the invention where a test swab 704 is scanned by the camera of a mobile device 702. In this embodiment, the mobile device 702 uses photo recognition to create collected test data based on the color 706 of the test swab 704. That is, if the test swab reacts with a targeted material to produce a specified color 706 indicating the presence of a toxin or other harmful material, then the mobile device 702 can create collected test data using photo recognition technology based on the color 706. It can be appreciated that this feature of the invention allows a user to quickly and accurately upload test information without having to understand what the color of a test swab indicate, thus avoiding the potential for uploading incorrect data. In another embodiment, the test strip reveals different shapes and/or alphabetical, numerical and/or alphanumeric characters, and the mobile device uses photo recognition to interpret the different shapes and/or characters to create collected test data.

According to embodiments of the invention, collected test data can be aggregated across specific data points within the group of: toxin(s); allergen(s), geographic location; time; date; user(s); user(s) personal data (such as age, gender, height, weight, nationality, ethnicity, lifestyle); or test area category, wherein test area category includes food, air, water, soil, consumer products, and self. A user can select specific test information such as air, food, water, soil, consumer products or self through various data point selectors. This information can then be displayed via numerous data screens. FIGS. 8-14 display various data screens which display different filters of the aggregated data.

Figure 8:
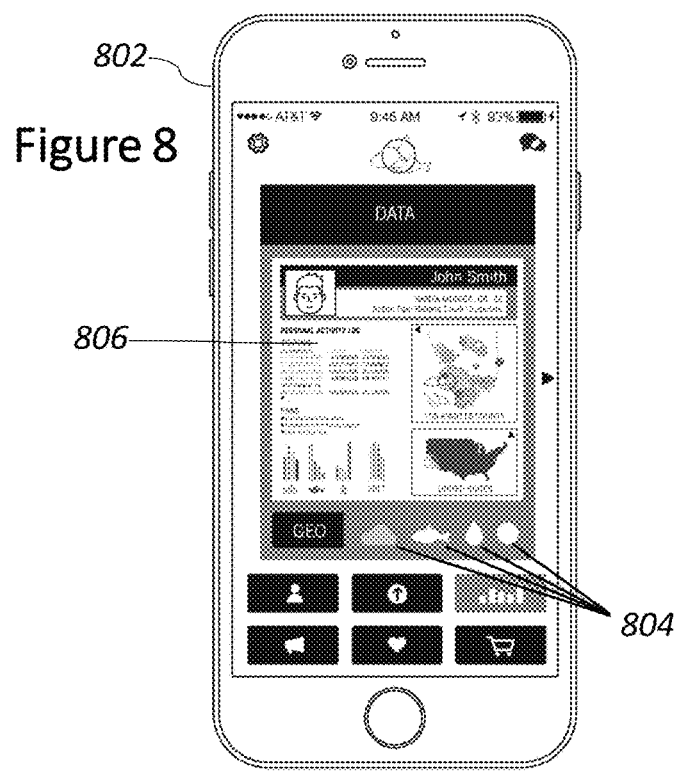
FIG. 8 illustrates an embodiment of the invention where a mobile device displays a personal map data screen.

FIG. 8 illustrates an embodiment of the invention where a mobile device 802 displays a personal map data screen. A user can select a specific test information such as air, food, water, or self through data point selectors 804. In an alternate embodiment, additional selectors will appear for the inclusion of soil and consumer products data. The personal map shows the user's account data, such as name, town, age, etc.; the user's personal activity log 806 (depicting information such as the date, time, globally geo-tracked location and results of each test performed); and the community action groups which the user has joined, wherein multiple users can collaborate on, and communicate regarding, the testing of particular areas of interest. In one embodiment, a user can view targeted areas of particular concern where test data shows environmental or biological issues. In another embodiment, users can create transformation objectives for the targeted areas and enroll users in targeted groups, wherein each targeted group is associated with a targeted area. In yet another embodiment, users can provide the targeted groups periodic updates including updated collected data and progress on achieving the transformation objective.

FIG. 9 illustrates an embodiment of the invention where a mobile device 904 displays a local map data screen 904. The local map data screen 904 pools and reveals the global data from all users on a local geographic level, all searchable and scrubbable locally, regionally, nationally or globally to reveal desired result profiles.

FIG. 10 illustrates an embodiment of the invention where a mobile device 1002 displays a global map data screen 1004. The global map data screen 1004 pools and reveals the global data from all users on a global geographic level, all searchable and scrubbable locally, regionally, nationally or globally to reveal desired result profiles.

FIG. 11 illustrates an embodiment of the invention where a mobile tablet device 1102 displays a global map data screen 1104. The global map data screen 1104 pools and reveals the global data from all users on a global geographic level, all searchable and scrubbable locally, regionally, nationally or globally to reveal desired result profiles.

Alternative embodiments allow a user to access data on wearable technology such as a smart watch. FIG. 12 illustrates an embodiment of the invention where a smart watch 1202 displays a global map data screen 1204. A user can select specific test information such as air, food, water, soil, consumer products or self through various data point selectors. The global map pools and reveals the global data from all users on a global geographic level, all searchable and scrubbable locally, regionally, nationally or globally to reveal desired result profiles.

Figure 13:
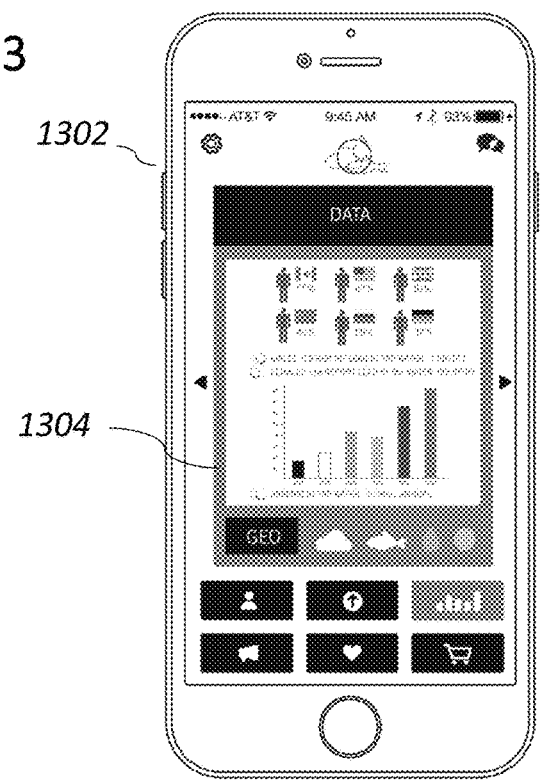
FIG. 13 illustrates an embodiment of the invention where a mobile device displays a trend data screen.

FIG. 13 illustrates an embodiment of the invention where a mobile device 1302 displays a trend data screen 1304. The trend data screen 1304 map pools and reveals the global data from all users on a global geographic level, all searchable and scrubbable locally, regionally, nationally or globally to reveal desired trend-related result profiles.

Figure 14:
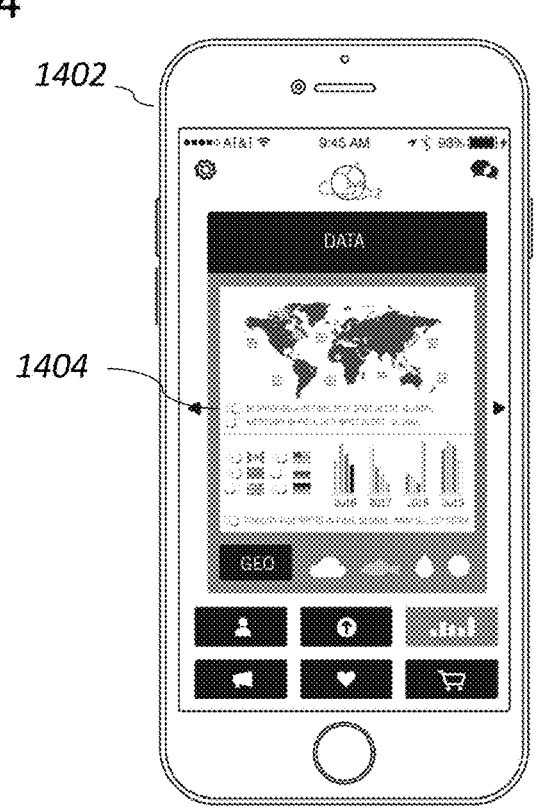
FIG. 14 illustrates an embodiment of the invention where a mobile device displays a hot spot data screen.

FIG. 14 illustrates an embodiment of the invention where a mobile device 1402 displays a hot spot data screen 1404. The hot spot data screen 1404 map pools and reveals the global data from all users on a global geographic level, all searchable and scrubbable locally, regionally, nationally or globally to reveal desired hot spot-related and/or ranked result profiles.

Figure 15:
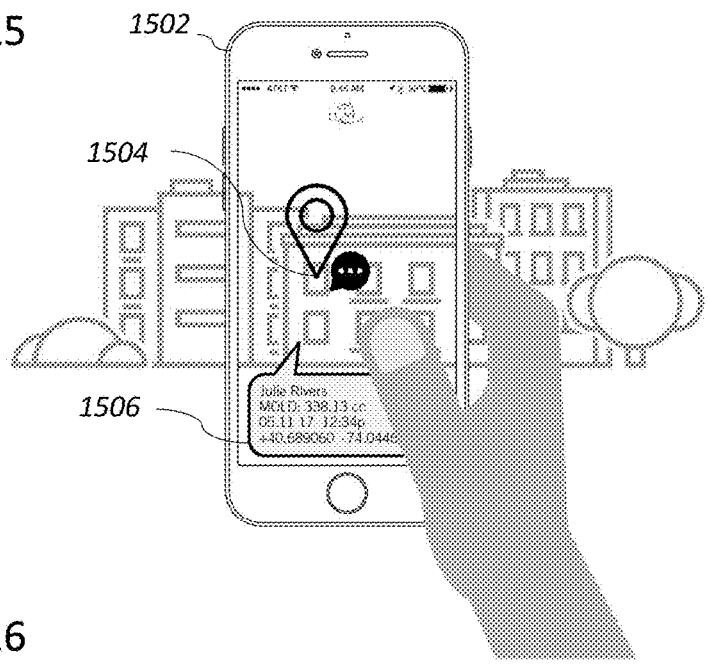
FIG. 15 illustrates an embodiment of the invention where a mobile phone displays an augmented reality overlay.

FIG. 15 illustrates an embodiment of the invention where a mobile phone 1502 displays an augmented reality overlay from a long or medium distance. A user can discover geoplotted data points 1504 on the augmented reality overlay. The augmented reality overlay will reveal geoplotted data points triggered by user test results globally. Those data points will reveal on the augmented reality overlay key data information such as the toxin or allergen, date, time, location, etc. Users will also be able to message each other regarding such data points and/or any other desired communication topics.

Figure 16:
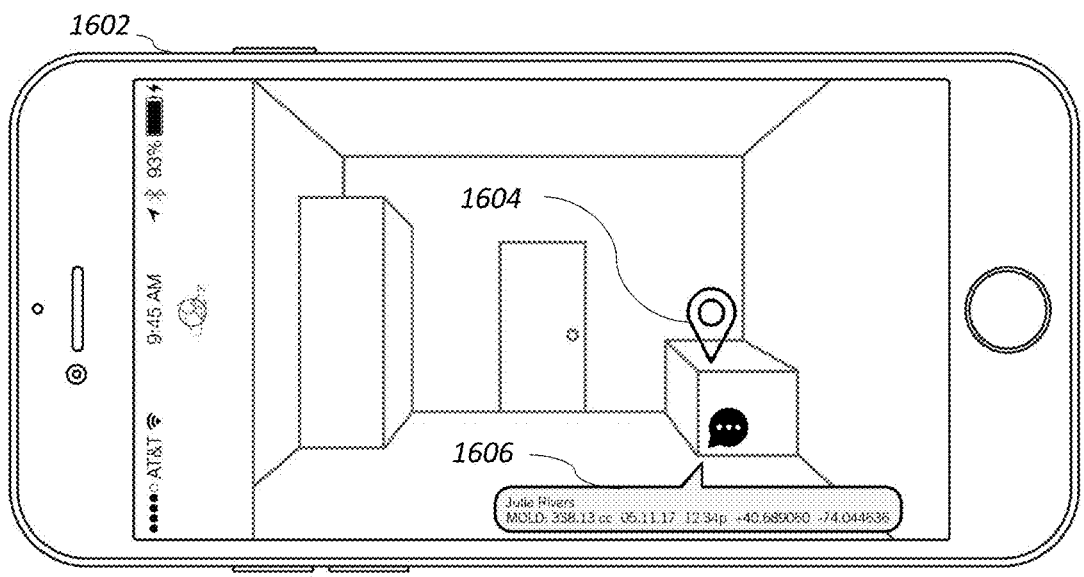
FIG. 16 illustrates an embodiment of the invention where a mobile phone displays an augmented reality overlay.

FIG. 16 illustrates an embodiment of the invention where a mobile phone 1602 displays an augmented reality overlay from a short distance. A user can discover geoplotted data points 1604 on the augmented reality overlay. The augmented reality overlay will reveal geoplotted data points 1604 triggered by user test results globally. Those data points will reveal on the augmented reality overlay key data information 1606 such as the toxin or allergen, date, time, location, etc. Users will also be able to message each other regarding such data points and/or any other desired communication topics.

Figure 17:
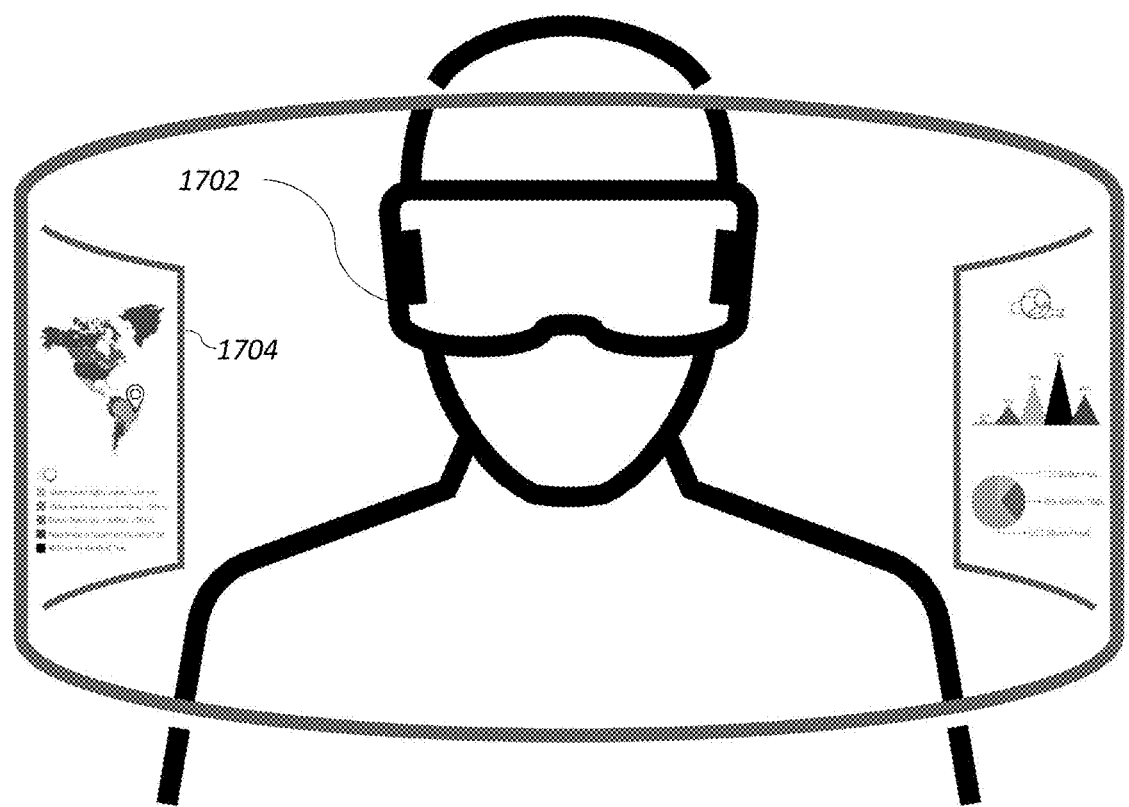
FIG. 17 illustrates an embodiment of the invention where a virtual reality headset is worn by a user to view aggregated test data.

FIG. 17 illustrates an embodiment of the invention where a virtual reality headset 1702 is worn by a user to view aggregated test data 1704, including information and data from personal profile(s), upload screens, data screens (personal map, local map, global map, trend data, hot spots) and other pertinent information.

Figure 18:
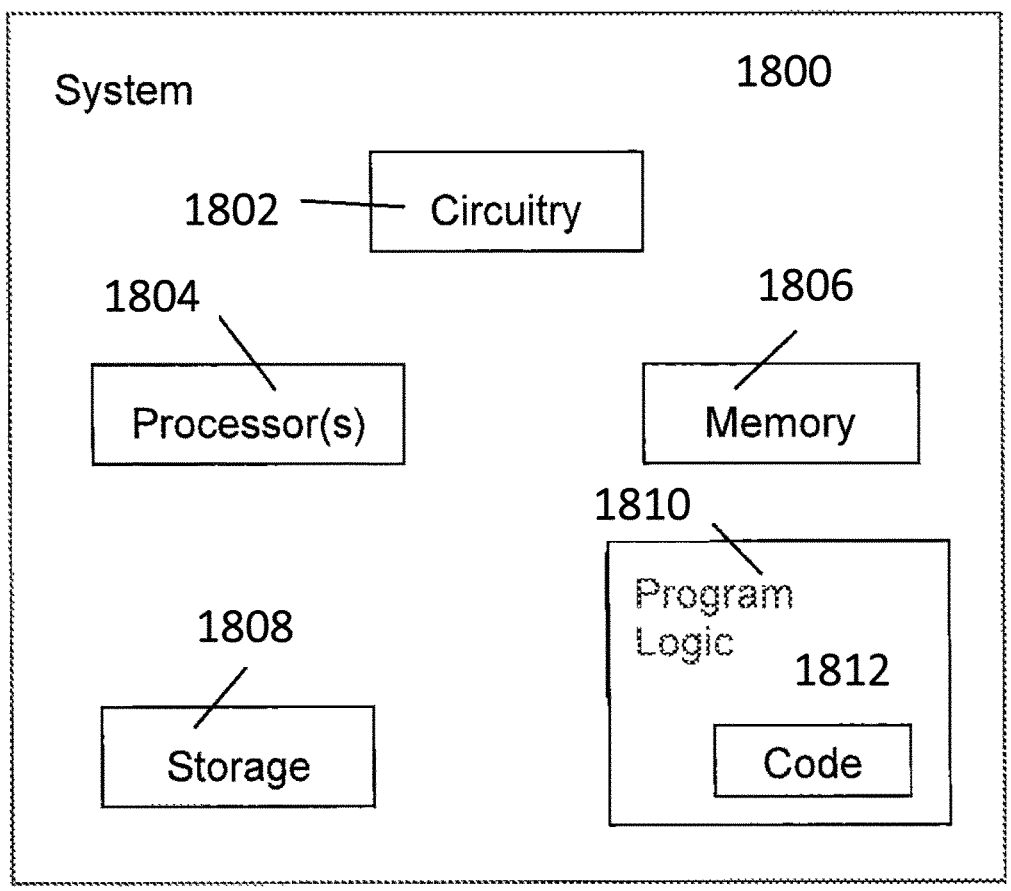
FIG. 18 illustrates a block diagram of a computer system 1800 which is part of the technical architecture of certain embodiments of the present invention.

FIG. 18 illustrates a block diagram of a computer system 1800 which is part of the technical architecture of certain embodiments of the present invention. The system 1800 may include a circuitry 1002 that may in certain embodiments include a microprocessor 1804. The computer system 1800 may also include a memory 1806 (e.g., a volatile memory device), and storage 1808. The storage 1808 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 1808 may comprise an internal storage device, an attached storage device and/or a network accessible storage device. The system 1800 may include a program logic 1810 including code 1812 that may be loaded into the memory 1806 and executed by the microprocessor 1804 or circuitry 1802.

In certain embodiments, the program logic 1810 including code 1812 may be stored in the storage 1808. In certain other embodiments, the program logic 1810 may be implemented in the circuitry 1802. Therefore, while FIG. 18 shows the program logic 1810 separately from the other elements, the program logic 1810 may be implemented in the memory 1006 and/or the circuitry 1002.

One or more aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

In addition to the above, one or more aspects of the present invention may be provided, offered, deployed, managed, serviced, etc. by a service provider who offers management of customer environments. For instance, the service provider can create, maintain, support, etc. computer code and/or a computer infrastructure that performs one or more aspects of the present invention for one or more customers. In return, the service provider may receive payment from the customer under a subscription and/or fee agreement, as examples. Additionally or alternatively, the service provider may receive payment from the sale of advertising content to one or more third parties.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiment with various modifications as are suited to the particular use contemplated.

Although the present invention has been described in relation to particular embodiments thereof, many other variations and modifications will become apparent to those skilled in the art. As such, it will be readily evident to one of skill in the art based on the detailed description of the presently preferred embodiment of the system and method explained herein, that different embodiments can be realized.

The invention claimed is:

1. A method for detecting, measuring, storing, analyzing and enabling access to collected biological or environmental test data, the method comprising:
   a) providing one or more test packs comprising one or more testing mediums for testing biological or environmental materials;
   b) testing, via the one or more testing mediums, a targeted material at a targeted location, wherein the one or more testing mediums reacts with the targeted material to reveal information including a scannable element;
   c) scanning, via a scanning device connected to a computer network, the one or more testing mediums to create collected test data based on the scannable element, wherein the scanning takes place a short time after the testing and at the targeted location, and wherein the collected test data includes the time, date and geographical tracking data based on the GPS location of the scanning device at the time of the scanning;
   d) sending, via the scanning device, the test data to a remote database located on a remote server;
   e) enabling remote access to the test data in the remote database;
   f) accessing, via an accessing device connected to the remote server, the remote database to view information about areas of concern.

2. The method of claim 1, further comprising aggregating the collected test data across specific data points, wherein test area category includes food, air, water, soil, consumer products and self.

3. The method of claim 2, further comprising listing, based on geographic location, targeted areas of particular concern where test data shows environmental or biological issues.

4. The method of claim 3, wherein the test packs comprise a specific bundle of testing mediums directed towards a goal objective.

5. The method of claim 4, further comprising creating transformation objectives for the targeted areas and enrolling users in targeted groups wherein each targeted group is associated with a targeted area.

6. The method of claim 5, further comprising providing the targeted groups periodic updates including updated collected data and progress on achieving the transformation objective.

7. The method of claim 6, wherein the scanning device is a mobile phone, mobile tablet device, smart watch, smart wearable, virtual reality or augmented reality headset.

8. The method of claim 7, wherein the testing strips reveal bar codes based on the testing and the scanning is performed by reading the testing strip bar code via a camera located on the scanning device to create the collected test data.

9. The method of claim 7, wherein the scannable element further comprises specific colors based on the reaction and the scanning is performed by taking a photo of the strip and recognizing the color to create the collected test data.

10. The method of claim 7, wherein the scannable element further comprises specific alphabetical, numerical, or alphanumeric shapes based on the testing and the scanning is performed by taking a photo of the strip and recognizing the shape to create the collected test data.

11. The method of claim 7, wherein the targeted material tested is part of a consumer product and, and wherein the scanning step further comprises scanning a barcode on a container of the consumer product and adding the container barcode to the collected test data.

12. A system for storing, analyzing and enabling access to collected biological or environmental test data, the system comprising:
- (a) one or more test packs comprising one or more testing mediums for testing biological or environmental materials, wherein the one or more testing mediums reacts with a targeted material to reveal information including a scannable barcode element;
- (b) a scanning interface in communication with the test packs, wherein the scanning interface comprises a processor for scanning the one or more testing surfaces to create collected test data and electronically sending the test data to a remote database within a short time after the testing;
- (c) an access system for enabling remote access to the test data in the remote database (d) a plurality of accessing entities, wherein the accessing entities comprise processors for viewing the test data.

\* \* \* \* \*